US00PP15573P2

(12) United States Plant Patent
Olesen et al.

(10) Patent No.: US PP15,573 P2
(45) Date of Patent: Feb. 22, 2005

(54) MINIATURE ROSE VARIETY 'POULRA019'

(50) Latin Name: *Rosa hybrida*
Varietal Denomination: POULra019

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 158 days.

(21) Appl. No.: 10/336,053

(22) Filed: Jan. 3, 2003

(51) Int. Cl.[7] ..... A01H 5/00
(52) U.S. Cl. ..... Plt./122
(58) Field of Search ..... Plt./122

(56) References Cited

U.S. PATENT DOCUMENTS

PP13,275 P2 * 11/2002 Olesen et al. ..... Plt./121

OTHER PUBLICATIONS

UPOV ROM GTITM Computer Database, GTI Jouve Retrieval Software 2003/03 Citation(s) for 'POULra019'.*

* cited by examiner

*Primary Examiner*—Bruce R. Campell
*Assistant Examiner*—W. C. Haas

(57) ABSTRACT

A new miniature rose plant which has abundant, red flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification: Botanical: *Rosa hybrida* 'POULra019'. Commercial: Miniature.

SUMMARY OF THE INVENTION

The present discovery constitutes a new and distinct variety of a miniature pot rose plant which was discovered in a cultivated area. The mutation resulted from 'POULra002', a miniature pot rose hybridized by the same inventors. 'POULra002' is described and illustrated in U.S. Plant Pat. No. 13,275, and issued on Nov. 26, 2002. The new rose variety resulted from a naturally occurring mutation of unknown causation on a branch of 'POULra002'.

The rose plant of the present discovery has a unique combination of characteristics which are outstanding in the new variety and which distinguish it from the original rose 'POULra002' as well as all other varieties which we are aware of. For example, the new variety has:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type known to the inventors, and distinguish 'POULra019' from all other varieties of which we are aware.

The resulting mutation was selected and evaluations were conducted on the resulting rose plants in a controlled environment.

Asexual reproduction of 'POULra019' by cuttings and traditional budding was first done by L. Pernille and Mogens N. Olesen in their nursery in Fredensborg, Denmark in July of 1998. This initial and other subsequent propagations conducted in controlled environments have demonstrated that the characteristics of 'POULra019' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra019'. Specifically illustrated in the drawing:

1. Stem showing branching and the attachment of leaves, buds, and peduncles;
2. Flower bud, partially opened bud, and open bloom;
3. Flower petals, detached;
4. Sepals, receptacle, and pedicel;
5. Stem as well as a bare stem exhibiting thorns;
6. Leaves.

DETAILED DESCRIPTION OF THE VARIETY

The following is a description of 'POULra019', as observed in its growth in 10.5 cm pots under normal glasshouse growing conditions in Burlington, Canada. Observed plants are 9 weeks of age. Color references are made using The Royal Horticultural Society (London, England) Colour Chart, 1995, except where common terms of color are used.

For a comparison, several physical characteristics of the rose variety 'POULra002', a rose variety from the same inventors described and illustrated in U.S. Plant Pat. No. 13,275 and issued on Nov., 26, 2002 are compared to 'POULra019' in Chart 1.

CHART 1

| | 'POULra019' | 'POULra002' |
|---|---|---|
| Bud color | Red Group 53B. | Red Group 47B. |
| Petalage | 13 to 15. | 35 to 45. |
| Thorn color | Yellow-Green Group 150D. | Greyed-Red Group 180D. |

Origin of the claimed plant: Sport of 'POULra002'.

FLOWER AND FLOWER BUD

Blooming habit: Continuous.

Flower bud:

*Size.*—Upon opening, 22 mm in length from base of receptacle to end of bud. Bud Diameter is 14 mm.

*Bud form.*—Pointed ovoid.

*Bud color.*—As sepals unfold, Red Group 53B. At ¼ opening, Red Group 53B.

*Sepals.*—Upper surface: Green Group 143A. Lower surface: Green Group 143B. Strong foliaceous appendages on three of the five sepals. Surfaces of sepals slightly pubescent. Stipitate glands are present in small quantities. Shape: General shape of sepals is subulate. Base is flat at union with receptacle. Margin: Elliptical foliaceous appendages extend outward 5 to 9 mm at the base and middle zone of the sepal. At the sepal apex, foliaceous appendages less extensive, characterized as serrations. Size: 22 mm long×5 mm wide.

*Receptacle.*—Surface: Smooth. Shape: Urn-shaped. Size: 8 mm (h)×6 mm (w). Color: Green Group 143C.

*Peduncle.*—Surface: Stipitate glands and prickles observed. Length: 40 to 50 mm average length. Diameter: 3 mm. Color: Yellow-Green Group 144C. Strength: Weak.

*Borne.*—Singly.

*Anthocyanin.*—None observed.

Flower bloom:

*Fragrance.*—Moderate. Floral.

*Duration.*—As a pot plant, flowers last from 14 to 18 days. Petals fall cleanly away from plant.

*Size.*—Average flower diameter is 40 mm when open. Flower depth is 20 to 23 mm from petal edges to the top of the receptacle.

*Form.*—Shape of flower when viewed from the side: Upon opening, upper part: Flattened convex. Upon opening, lower part: Convex. Open flower, upper part: Flattened convex. Open flower, lower part: Convex.

*Petalage.*—Average range: 13 to 15 petals under normal conditions with 3 to 5 petaloids.

Color:

*Upon opening, petals.*—Outermost petals: Outer side: Red Group 53B. Inner Side: Red Group 53B. Innermost petals: Outer Side: Red Group 53B. Inner Side: Red Group 53B.

*Upon opening, basal petal spots.*—Outermost petals: Outer Side: White Group 155A. Inner Side: White Group 155A. Innermost petals: Outer Side: White Group 155A. Inner Side: White Group 155A.

*After opening, petals.*—Outermost petals: Outer Side: Red Group 53B. Inner Side: Red Group 53B. Innermost petals: Outer Side: Red Group 53B. Inner Side: Red Group 53B.

*After opening, basal petal spots.*—Outermost petals: Outer Side: White Group 155C. Inner Side: White Group 155C. Innermost petals: Outer Side: White Group 155C. Inner Side: White Group 155C.

General tonality: On open flower Red Group 53B. No change in the general tonality at the end of the 14$^{th}$ day. Afterwards, general tonality is Red-Purple Group 57B.

Petals:

*Petal reflex.*—Moderate.

*Petal edge.*—Entire.

*Shape.*—Round.

*Petaloids.*—Quantity: 3 to 5. Size: 15 mm long; 9 mm wide. Color: Red Group 53B on both upper and lower surfaces. Shape: Irregular in shape. The base is acute, while the apex is rounded, typically with a cleft.

*Thickness.*—Average.

*Arrangement.*—Not formal.

*Petal dimensions.*—23 mm long×21 mm wide.

*Surface texture.*—Smooth.

Reproductive organs:

*Pollen.*—Color: Yellow Group 11B. Quantity: Scant.

*Anthers.*—Size: 1.25 mm long. Color: Greyed-Yellow Group 162A. Quantity: 75.

*Filaments.*—Color: Yellow-Green Group 144D at base, White Group 155A at middle, Red-Purple Group 62C. Length: 6 mm.

*Stigmas.*—Even in relation to the length of the filaments and the height of the anthers. Color: Yellow-White Group 158B. Quantity: Typically 30–35. 31 Observed.

*Styles.*—Color: Yellow-Green Group 150D. Quantity: Typically 30–35. 31 Observed.

*Seed formation.*—No hips observed.

PLANT

Plant growth: Vigorous, compact. When grown as a 10 cm pot plant, the average height of the plant is 20 cm and the average width is 20 cm.

Stems:

*Color.*—Young wood: Yellow-Green Group 144A. Older wood: Yellow-Green Group 144A.

*Length.*—110 mm.

*Diameter.*—2.5 mm.

*Internodes.*—Distance between nodes is 25 mm on average.

*Prickles.*—Incidence: 5 thorns per 10 cm of stem. Size: Average length: 3 mm. Color: Yellow-Green Group 150D. Shape: Concave.

*Surface.*—Young wood: Smooth. Older wood: Smooth.

Plant foliage: Normal number of leaflets on leaves in middle of the stem: 5 leaflets.

*Compound leaf size.*—75 mm in length by 50 mm wide.

*Quantity.*—Average. 4 leaves per 10 cm of stem.

*Color.*—Upper Leaf Surface: Green Group 137A. Lower Leaf Surface: Green Group 138B.

*Juvenile foliage.*—Green Group Upper Leaf Surface: Yellow-Green Group 144A. Lower Leaf Surface: Yellow-Green Group 144A.

*Anthocyanin intonation.*—Location: Leaflet margins of juvenile foliage. Color: Greyed-Red Group 181A.

Plant leaves and leaflets:

*Stipules.*—Size: 8 mm long. Quantity: 2 stipules per compound leaf. Color: Yellow-Green Group 144A. Shape: Linear with outward extending apecies 5 mm in length. Margins: Finely serrated with stipitate glands in medium quantity observed.

*Petiole.*—Length: 18 mm. Diameter: 1 mm. Color: Yellow-Green Group 144A. Underneath: Yellow-Green Group 144A. Margins: Yellow-Green Group 144A. Anthocyanin: Greyed-Red Group 178A.

*Rachis.*—Length: 20 mm.

*Leaflet.*—Edge: Serrated. Size: 28 mm in length by 18 mm wide. Shape: Generally Ovate. Apex shape is acute. Base shape is round. Texture: Thin. Glossiness: Matte. Arrangement: Odd pinnate. Venation: Reticulate. Veins are predominantly Yellow-Green Group 145B. The central leaf vein exhibits anthocyanic pigment the color of Greyed-Red Group 181B.

Disease resistance: Average resistance to mildew, black spot, and Botrytis under normal growing conditions in Burlington, Canada.

It is claimed:

1. A new and distinct variety of rose plant of the miniature class, substantially as herein illustrated and described as a distinct and novel rose variety due to its abundant, red flowers, vigorous growth, compact habit, suitability for production from softwood cuttings in pots, and durable flowers and foliage which make the variety suitable for distribution in the floral industry.

* * * * *

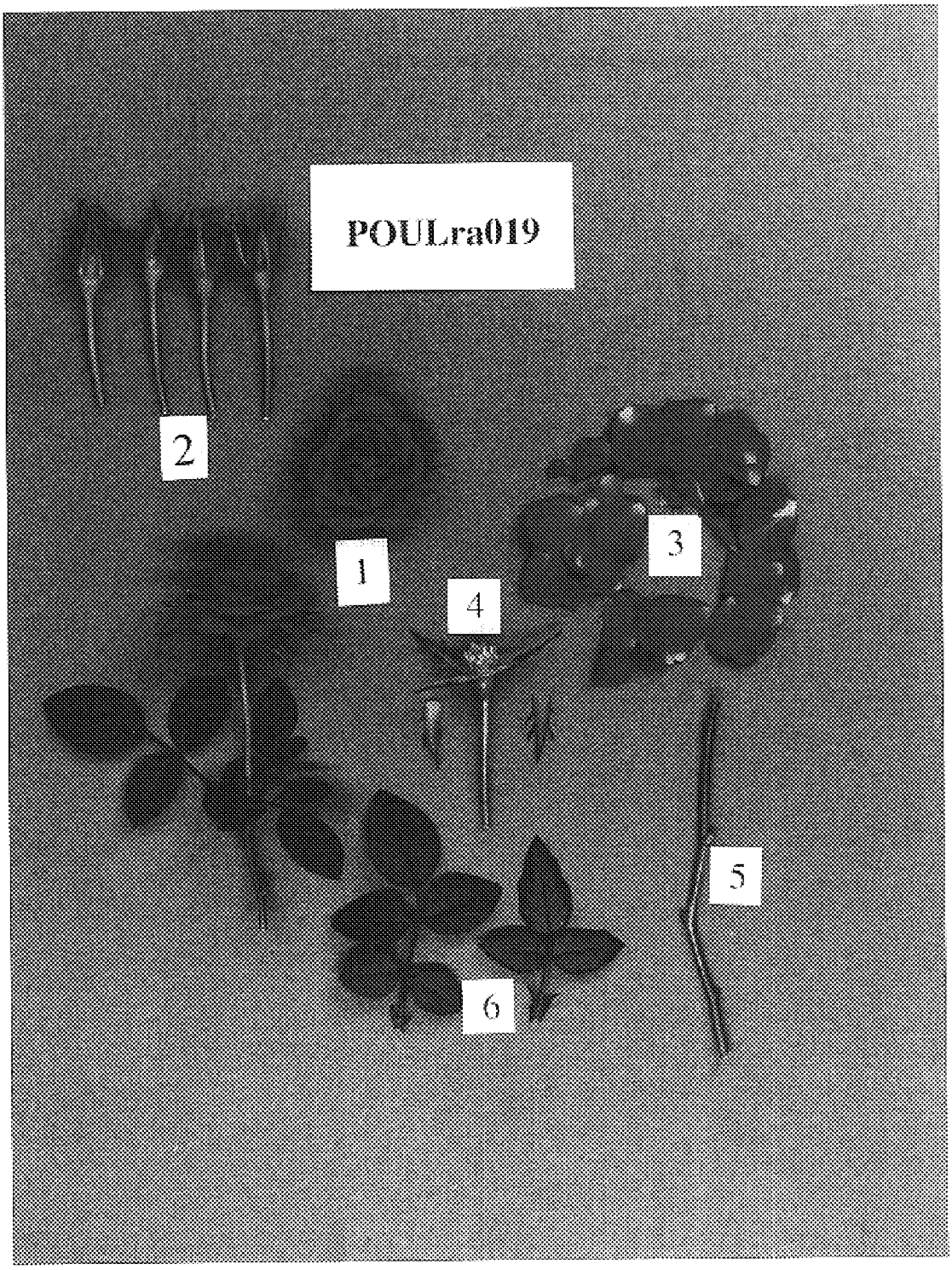
POULra019
2
1
4
3
5
6